(12) United States Patent
Bates et al.

(10) Patent No.: US 10,296,711 B2
(45) Date of Patent: May 21, 2019

(54) CLIENT-SERVER MULTIMEDIA ARCHIVING SYSTEM WITH METADATA ENCAPSULATION

(75) Inventors: Allen Keith Bates, Tucson, AZ (US); Louie Arthur Dickens, Tucson, AZ (US); Timothy A. Johnson, Tucson, AZ (US); Craig Anthony Klein, Redington Beach, FL (US); Yun Mou, Tucson, AZ (US); Stephen Leonard Schwartz, Tucson, AZ (US); Anna W. Topol, Jefferson Valley, NY (US); Daniel James Winarski, Tucson, AZ (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 837 days.

(21) Appl. No.: 12/781,809

(22) Filed: May 17, 2010

(65) Prior Publication Data

US 2011/0282844 A1 Nov. 17, 2011

(51) Int. Cl.
*G06F 17/30* (2006.01)
*G16H 30/20* (2018.01)
*G06F 19/00* (2018.01)

(52) U.S. Cl.
CPC ...... *G06F 19/321* (2013.01); *G06F 17/30073* (2013.01); *G16H 30/20* (2018.01)

(58) Field of Classification Search
CPC .......................... G06F 17/30073; G16H 30/20
USPC ........ 707/661, 665, 667, 668, 670, 673, 941
See application file for complete search history.

(56) References Cited

U.S. PATENT DOCUMENTS

| 7,149,750 | B2 | 12/2006 | Chadwick |
| 7,734,584 | B1* | 6/2010 | McBarron ......... G06F 17/30067 707/622 |
| 7,913,053 | B1* | 3/2011 | Newland ....................... 711/172 |
| 2002/0080392 | A1 | 6/2002 | Parvulescu |
| 2003/0095712 | A1* | 5/2003 | Christ et al. ................... 382/232 |
| 2003/0174074 | A1* | 9/2003 | LoCasale ................ H03M 7/30 341/50 |
| 2004/0071038 | A1 | 4/2004 | Sterritt |
| 2004/0122872 | A1 | 6/2004 | Pandya et al. |

(Continued)

OTHER PUBLICATIONS

Wikipedia, gzip, https://web.archive.org/web/20080904063347/http://en.wikipedia.org/wiki/Gzip, Sep. 9, 2008, 3 pp.*

(Continued)

*Primary Examiner* — Marc S Somers
(74) *Attorney, Agent, or Firm* — Griffiths & Seaton PLLC

(57) ABSTRACT

A system, method and computer program product for archiving image, audio, and text data with metadata encapsulation in a client-server storage library is described. The server receives and holds the images, audio, or text to be archived in an image, audio or text logical partition which includes a directory of the images, audio, or text. The information is encapsulated in a metadata wrapper and stored in the library as a closed image, audio, or text file along with a closed copy of the directory. The closed image, audio, or text directory is also stored in the client. The images may be encapsulated in MXF, DICOM, Tape Archive (TAR) or GZIP formats. The storage library may have magnetic tapes, magnetic disks or optical disks as storage media.

16 Claims, 11 Drawing Sheets

(56) References Cited

U.S. PATENT DOCUMENTS

| | | |
|---|---|---|
| 2005/0177312 A1 | 8/2005 | Guerrant et al. |
| 2005/0223277 A1 | 10/2005 | Ballard |
| 2005/0240445 A1* | 10/2005 | Sutherland et al. ............... 705/3 |
| 2006/0010150 A1* | 1/2006 | Shaath et al. .................. 707/102 |
| 2006/0155670 A1* | 7/2006 | Forlenza et al. ................... 707/1 |
| 2007/0024752 A1* | 2/2007 | Roush ...................... H04N 5/45 |
| | | 348/565 |
| 2007/0038687 A1* | 2/2007 | Carroll et al. ................ 707/204 |
| 2007/0067364 A1* | 3/2007 | Barbian et al. ............... 707/204 |
| 2010/0049929 A1* | 2/2010 | Nagarkar et al. ............. 711/162 |
| 2010/0241615 A1* | 9/2010 | Marshall ................ G06Q 10/10 |
| | | 707/661 |

OTHER PUBLICATIONS

SMPTE Standard for Television—Material Exchange Format (MXF)—Fire Format Specification (Standard), Sep. 22, 2004, SMPTE 337M-2004, The Society of Motion Picture and Television Engineers, pp. 101.*

"Introduction to the Material Exchange Format", The MXF Book, Edited by Nick Wells, Focal Press, Elsevier, 2006.

Oosterwijk et al., "DICOM Basics", 3rd Edition, OTech, Inc., Aubrey, TX, 2002.

* cited by examiner

CLIENT-SERVER MULTIMEDIA ARCHIVING SYSTEM WITH METADATA ENCAPSULATION

FIELD OF THE INVENTION

The invention relates generally to data archiving in computers, and more particularly to a system, method and computer program product for storing and retrieving multimedia data in a client-server archive library with metadata encapsulation.

BACKGROUND

The availability of various computer-based devices and computer networks, and the growing amount of images and video contents being generated by computer applications in different fields, lead to a demand for efficient methods for archiving such data at remote data storage libraries.

As an example, in the medical field, a large amount of patient imaging data including X-rays, computed tomography images (CTI), magnetic resonance images (MRI), ultrasound video recordings, etc. are generated everyday at hospitals and medical clinics. The image and video data is often stored in a digital format to facilitate its handling, transmission, storing and retrieving. At the present, the Digital Imaging and Communications in Medicine (DICOM) format is a commonly used standard for handling medical images and video data.

Typically, images and video data come from decentralized workstations and client devices such as laptop computers, PDAs, workstations, as well as computers that are connected to an image-producing equipment like a MRI system at a hospital. These decentralized client computers often need to retrieve previously stored images and video data from a server and data archive library systems that are connected to the server for data archiving.

Current data archiving solutions typically use tape library systems where workstations and client devices are connected to one or more servers, and the servers are connected to one or more libraries. In large data centers, such as those providing imaging for health care, entertainment, weather, military, and space exploration applications, these servers and libraries are often interconnected in a grid computing environment. The computing grid allows much flexibility in the sharing of image and video data. However, the amount of data for archive and retrieval is staggering and in the Exabyte (1000 Petabyte) scale. To mitigate the unnecessary transfer of unwanted data during the search for specific data, the desired data must be identified based on information other than the data itself, before the entire set of images or video streams are retrieved from the tape library to the user. Such a technique for screening of data improves the overall performance and usability of the archive system.

From the foregoing, there still exists a need for an efficient system, method and computer program product for storing and retrieving image, video, and other multimedia data in a client-server archive library.

SUMMARY

The invention relates to archiving and retrieving multimedia data in a client-server library with metadata encapsulation. More particularly, the invention provides an efficient system and method for archiving image and video data from decentralized client computers. The server receives and holds the images to be archived in an image logical partition which includes a directory of the images. The images are encapsulated with their metadata before being stored in the library along with a closed copy of the image directory.

The details of the preferred embodiments of the invention, both as to its structure and operation, are described below in the Detailed Description section in reference to the accompanying drawings. The Summary is intended to identify key features of the claimed subject matter, but it is not intended to be used to limit the scope of the claimed subject matter.

DETAILED DESCRIPTION OF THE INVENTION

Figure 1A:
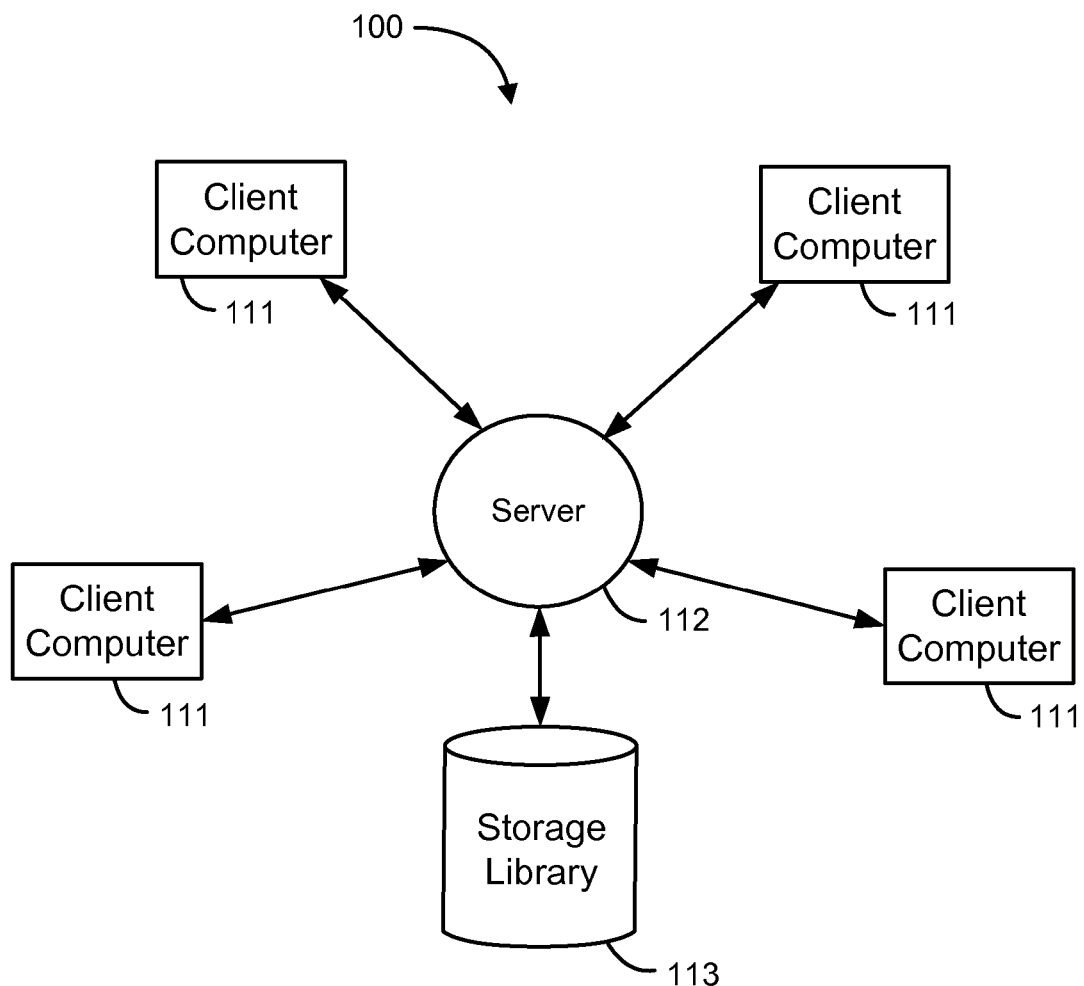
FIG. 1A is a block diagram illustrating a typical client-server library system for archiving data in which aspects of the invention can be implemented.

The present invention concerns a system, method and computer program product for archiving image and video data in a client-server storage library with image metadata encapsulation.

As will be appreciated by one skilled in the art, aspects of the present invention may be embodied as a method, system or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc. or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN), a wide area network (WAN), Ethernet, SCSI, iSCSI, Fibre Channel, Fibre Channel over Ethernet, and Infiniband, or the connection may be made to an external computer, for example, through the Internet using an Internet Service Provider.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures described below illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Referring now to the drawings and in particular to FIG. 1A, there is depicted a block diagram of client-server library system 100 for archiving data in which aspects of the invention may be implemented. The system 100 includes multiple client computers 111 from which images and video data are transmitted to a server 112 for archiving in a data storage library 113. The client computers 111 also retrieve previously archived images and video data from the library 113 through the server 112. The client computers 111 may be personal computers, portable devices (e.g., PDAs), workstations, IBM TS7720™ servers, or computers attached to various image and video producing equipment. The client computers 111 may be connected to the server 112 through a local area network such as an Ethernet network, or by SCSI, iSCSI, Fibre Channel, Fibre Channel over Ethernet, and Infiniband. Server 112 may be an IBM TS7740™ server, TS7720™ server, or other servers. Similarly, the data storage library 113 may be connected to the server 112 using a high data rate connection such as an optical or copper fiber channel, SCSI, iSCSI, Ethernet, Fibre Channel over Ethernet and Infiniband. As an example, the data storage library 113 may be an IBM TS3500™ tape library that is attached to an IBM Power Systems™ acting as a server 112.

Figure 1B:
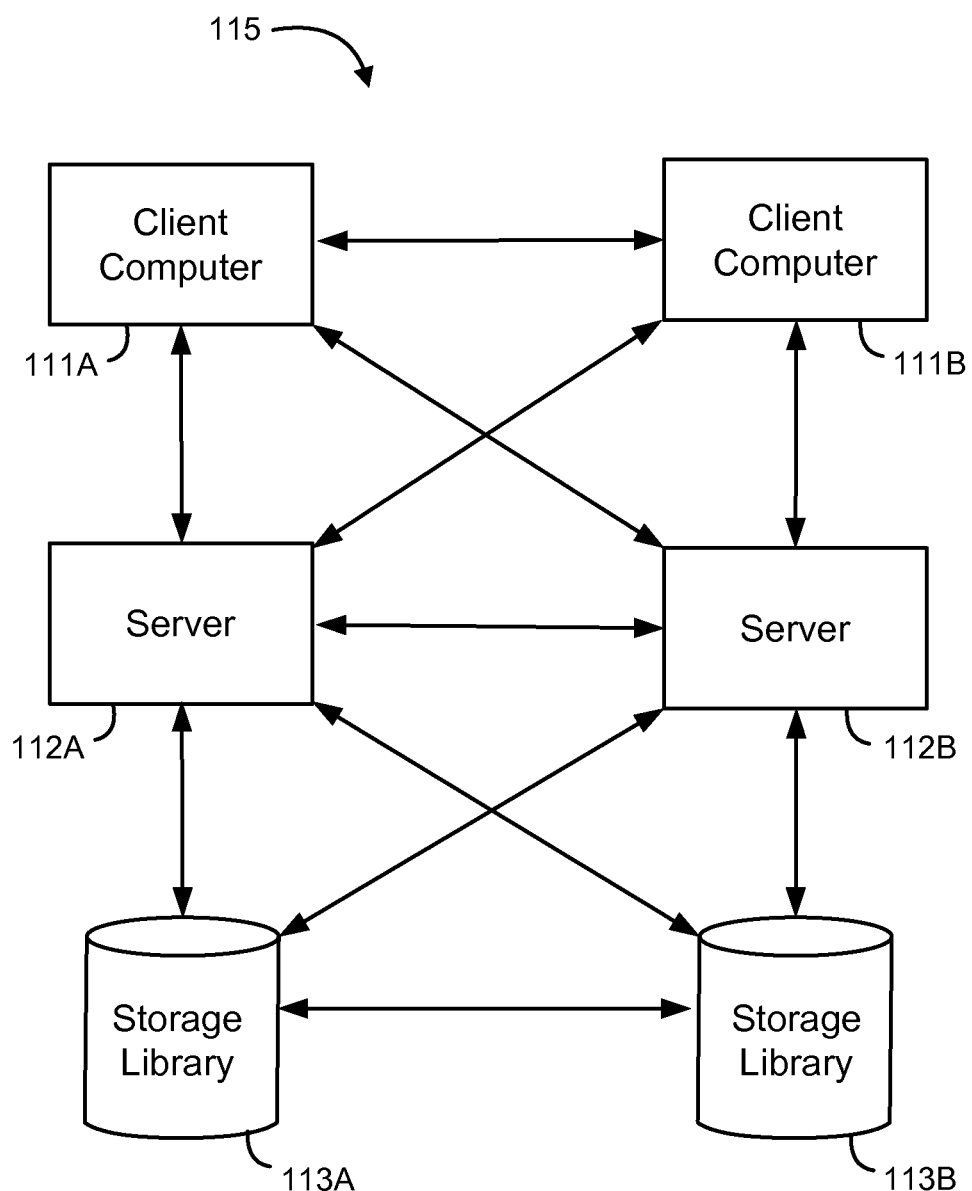
FIG. 1B is a block diagram illustrating a typical grid computing client-server library environment for archiving data in which aspects of the invention can be implemented.

FIG. 1B shows a block diagram of a typical grid computing library environment 115 for archiving data. The library environment 115 includes multiple client computers 111A and 111B which are interconnected to each other and to multiple servers 112A and 112B. The servers 112A and 112B are interconnected to each other and to multiple tape libraries 113A and 113B, which are also interconnected to each other.

Figure 2:
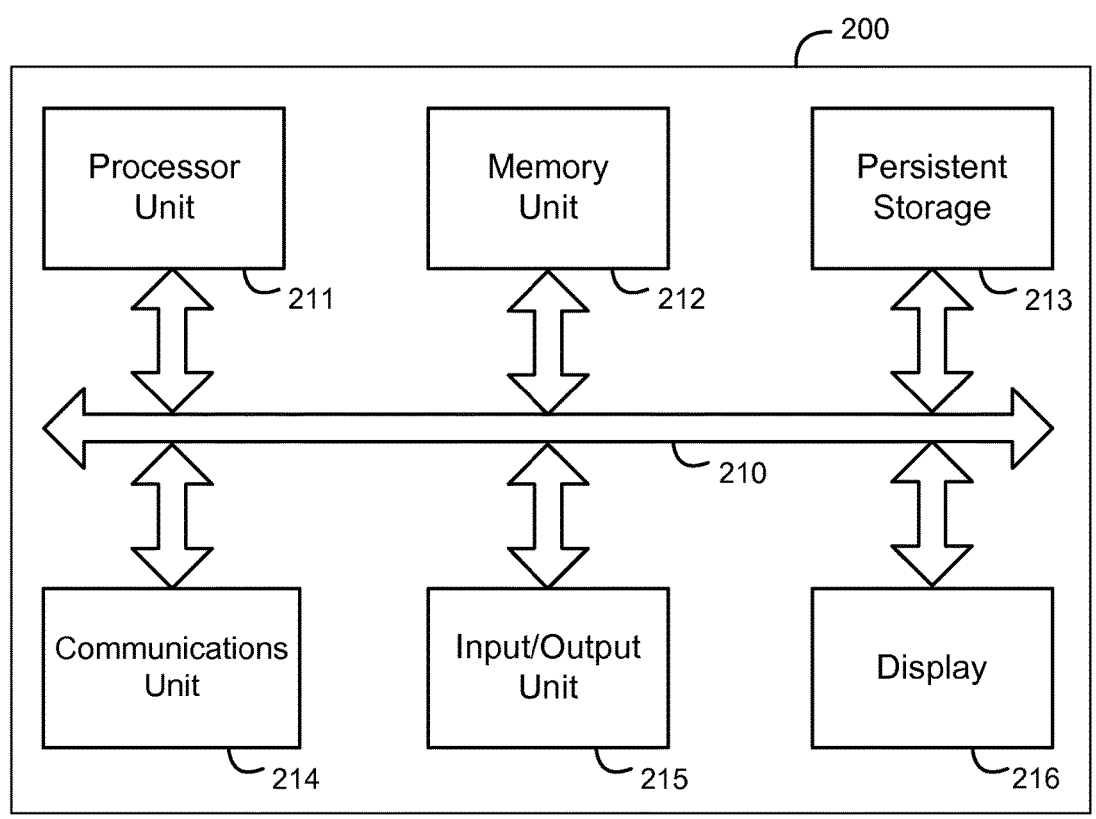
FIG. 2 is a block diagram showing a representative computer system which may be used as a client or a server computer.

FIG. 2 shows a block diagram of a data processing system that can be used as a client computer 111 or server computer 112. As shown, a data processing system 200 includes a processor unit 211, a memory unit 212, a persistent storage 213, a communications unit 214, an input/output unit 215, a display 216 and a system bus 210. Computer programs are typically stored in the persistent storage 213 until they are needed for execution, at which time the programs are brought into the memory unit 212 so that they can be directly accessed by the processor unit 211. The processor unit 211 selects a part of memory unit 212 to read and/or write by using an address that the processor 211 gives to memory 212 along with a request to read and/or write. Usually, the reading and interpretation of an encoded instruction at an address causes the processor 211 to fetch a subsequent instruction, either at a subsequent address or some other address. The processor unit 211, memory unit 212, persistent storage 213, communications unit 214, input/output unit 215, and display 216 interface with each other through the system bus 210.

Figure 3:
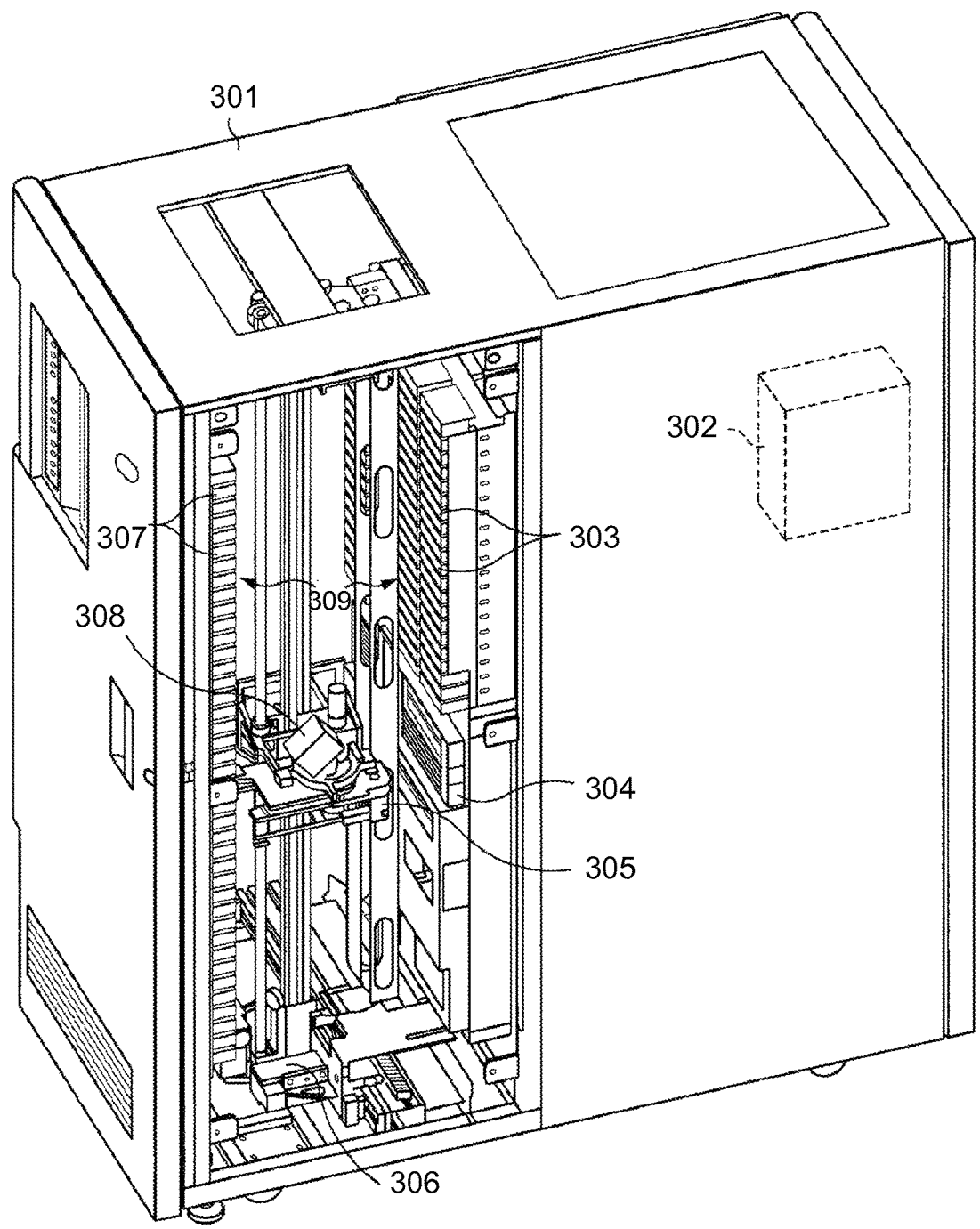
FIG. 3 illustrates a typical data storage tape library for archiving image and video data in accordance with aspects of the invention.

FIG. 3 illustrates an example of a data storage library 301 for use in the client-server image archiving system of the invention. The library 301 is an automated tape library that accommodates multiple tape drives 304 for reading and writing on tape media, such as single-reel or two-reel magnetic tape cartridges. Examples of the library 301 include IBM TS3400™ and TS3500™ Tape Libraries, IBM TotalStorage® 3494 Tape Libraries, and IBM 3952™ Tape Frames Model C20, which store magnetic tape cartridges and use IBM TS1130™ tape drives. Other examples of the library 301 include IBM TS3310™ and TS3100/3200™ tape libraries which store magnetic tape cartridges and use IBM LTO (Linear Tape Open) tape drives. A plurality of tape media 303 and 307 are stored in banks or groups of storage slots 309. Tape media may encompass a variety of media, such as that contained in magnetic tape cartridges, magnetic tape cassettes, and optical tape cartridges, in various formats. For universal reference to any of these types of media, the terms "tape media" or "media" are used herein, and any of these types of containers are referred to as "tape cartridges" or "cartridges" herein. An access robot 306, including a cartridge picker 305 and a bar code reader 308 mounted on the picker, transports a selected cartridge 303 and 307 between a storage slot 309 and a drive 304.

The library 301 further has a library controller 302 which includes at least one microprocessor. The library controller 302 may serve to provide an inventory of the cartridges 303 and to control the library 301. Typically, the library controller 302 has suitable memory and data storage capability to control the operation of the library 301. The library controller 302 controls the actions of the access robot 306, cartridge picker 305, and bar code reader 308. The library controller 302 is interconnected through an interface to one or more host processors, which provides commands requesting access to particular tape media or to media in particular storage slots. A host, either directly, or through the library controller, controls the actions of the data storage drives 304. Commands for accessing data or locations on the tape media and information to be recorded on, or to be read from, selected tape media are transmitted between the drives 304 and the host. The library controller 302 is typically provided with a database for locating the tape cartridges 303 in the appropriate storage slots 309 and for maintaining the cartridge inventory.

Figure 4:
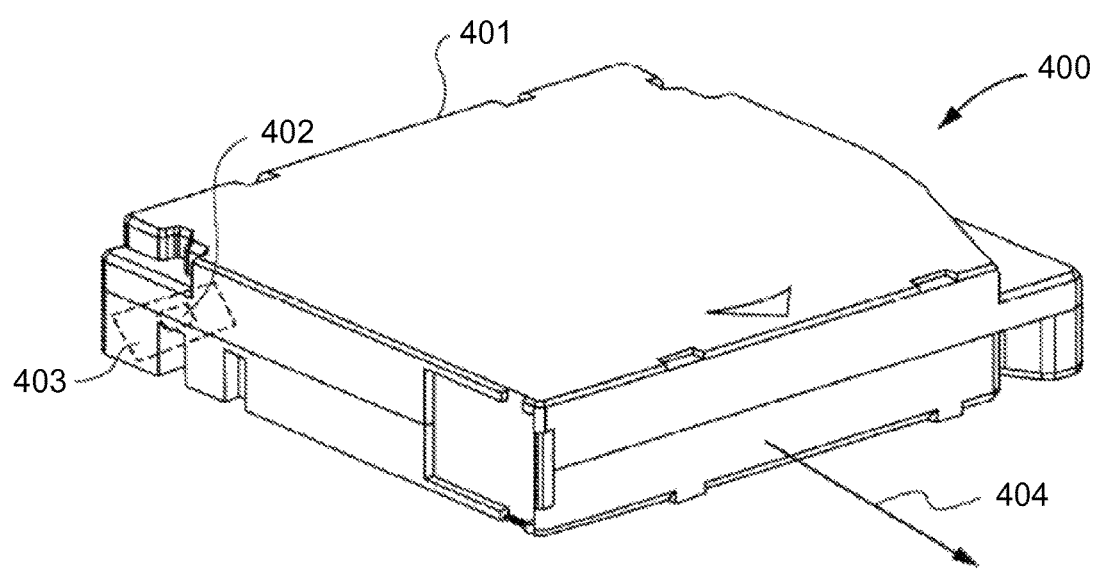
FIG. 4 illustrates an example of a tape cartridge for use in the data storage tape library in FIG. 3.

FIG. 4 illustrates a perspective view of an exemplary tape cartridge 400 for use in a tape drive system 304 of FIG. 3. The tape cartridge 400 has a reel (not shown) for holding tape media 401 (not shown), which is wound around the reel hub. The tape cartridge 400 further includes an RFID cartridge memory 402, which is on printed circuit board 403, for wireless interfacing with the tape drive 304 and the cartridge picker 305. The tape cartridge 400 is referred to as a single-reel cartridge as it includes only one tape reel which acts as a supply reel during operation. A take-up reel is provided in the tape drive 304 for receiving the tape media when the tape media is being unspooled from the tape reel. In a different design of the tape drive 304, a take-up reel might be included in the cartridge 400 itself rather than in the tape drive 304. Such a tape cartridge is referred to as a dual-reel cartridge. Cartridge 400 is inserted along direction 404 into tape drive 304.

Figure 5:
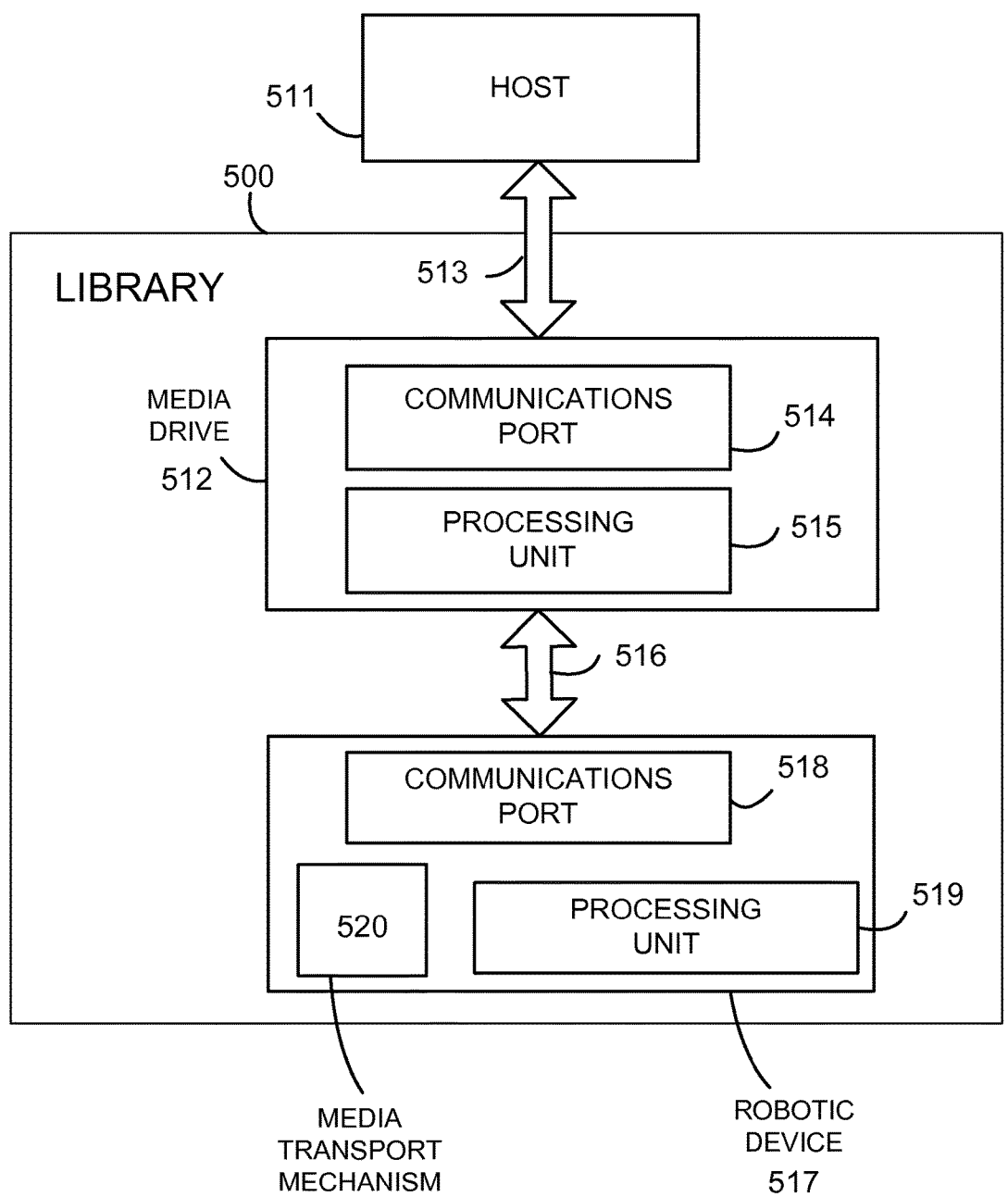
FIG. 5 is a block diagram showing an exemplary data storage tape library in communication with a host computer for providing aspects of the invention.

FIG. 5 is a block diagram showing the functional components of an exemplary data storage tape library 500 in communication with a host computer 511 for providing aspects of the invention. The library 500 is attached to a host 511, and includes a media drive 512 and a robotic device 517. Data and control path 513 interconnects the host 511 and drive 512. Similarly, data and control path 516 interconnects the drive 512 and the robotic device 517. The paths 513 and 516 may comprise suitable means for conveying signals, such as a bus with one or more conductive members (such as wires, conductive traces, cables, etc.), wireless communications (such as radio frequency or other electromagnetic signals, infrared communications, etc.), and fiber optic communications. Furthermore, the paths 513 and 516 may employ serial, parallel, or another communications format, using digital or analog signals as desired. Communications with the media drive 512 and robotic device 517 are through communications ports 514 and 518, respectively.

Both the drive 512 and the robotic device 517 include respective processing units 515 and 519. The library 500 manages the positioning and access of removable or portable data storage media such as magnetic tape, cartridge 400, optical tape, optical disk, removable magnetic disk drive, CD-ROM, digital video disk (DVD), or another appropriate format. Some of these types of storage media may be self-contained within a portable container, or cartridge. For universal reference to any of these types of storage media, this disclosure refers to them as media.

The host 501 may be a server, workstation, personal computer, or other means for exchanging data and control signals with the media drive 512. The drive 512 comprises a machine for reading data from and/or writing data to exchanging data with a portable data storage media. The robotic device 517 includes the processing unit 519 and a media transport mechanism 520 coupled to processing unit 519. The media transport mechanism 520 includes servos, motors, arms, grippers, sensors and other robotic, mechanical and electrical equipment to perform functions that include (at least) the transportation of media items between the drive 512, various storage bins (not shown), import/export slots, etc. The mechanism 520 may, for example, comprise an auto-loader mounted to the drive 512, a robotic arm housed inside a mass storage library, or another suitable device. As an example, the mechanism 520 may comprise an access robot 306, cartridge picker 305 and bar code reader 308 from FIG. 3.

Figure 6:
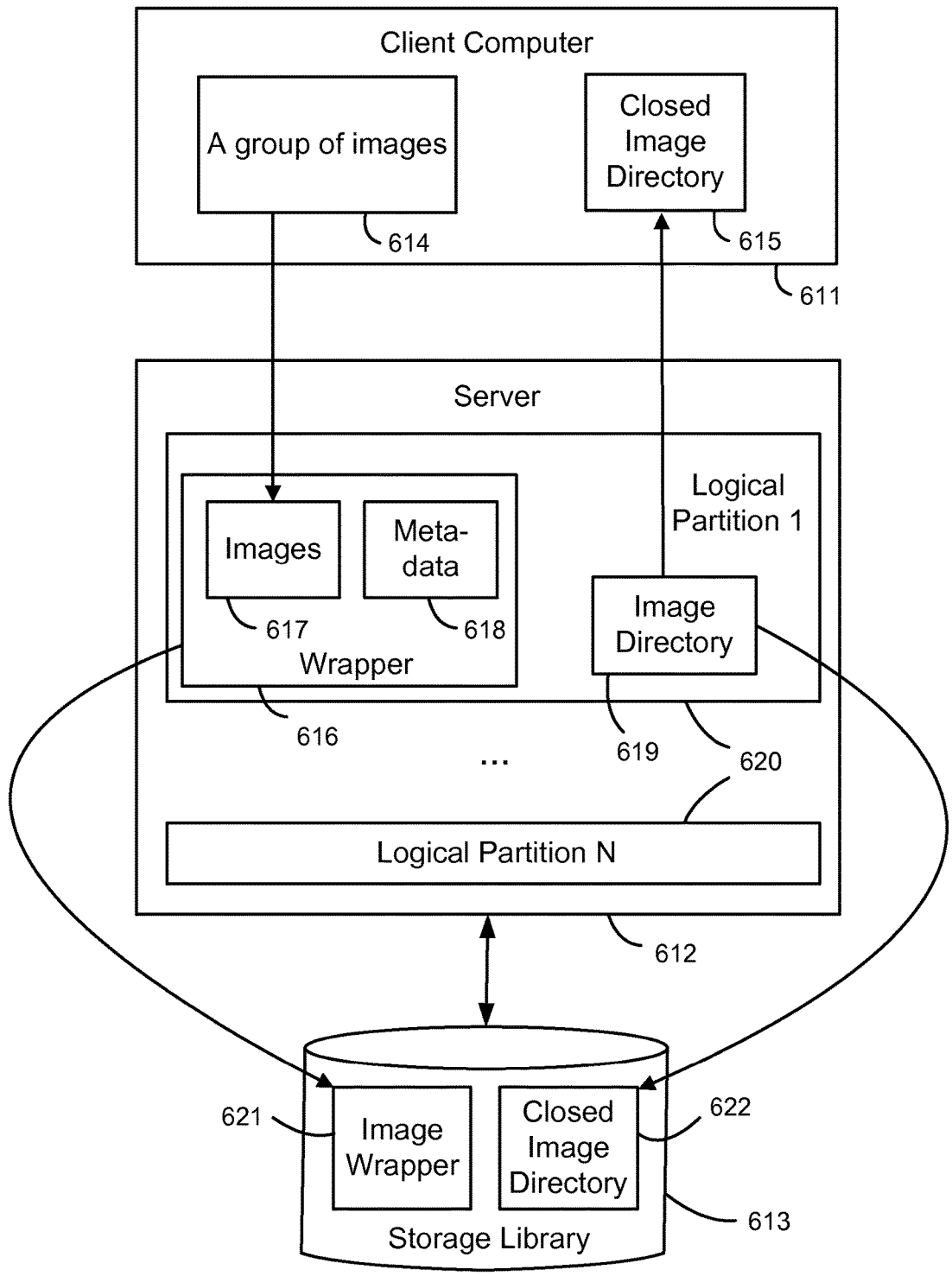
FIG. 6 is a block diagram illustrating an exemplary embodiment of the client-server storage library system for archiving image and video data in accordance with aspects of the invention.

FIG. 6 is a block diagram illustrating an exemplary embodiment of the client-server storage library system for archiving multimedia data, according to aspects of the invention. As an example, the illustrated embodiment is for archiving image and video data. Client computer 611 is one of the clients 111 in FIG. 1. The client 611 has a group of images 614 to be archived in data storage library 613. A server 612 receives the group of images 614 from client 611 and holds the images 614 in one of logical partitions 620, such as logical partition 1. As described below in reference to FIGS. 9-10, the logical partition 1 further maintains an image directory 619. Once the image group 614 is stored in a logical partition 620, the server encapsulates the images 614 in an image wrapper 616 that includes images themselves (617) and metadata 618 about the images 614. After the image encapsulation is completed, the server 612 closes the image directory 619 and saves the image wrapper 621 and a closed copy 622 of the image directory 619 in the storage library 613. A closed copy 615 of the image directory 619 is also stored in the client computer 611.

Metadata

Metadata 618 describes the definition, structure and administration of data files with all contents in context to facilitate future use of the captured and archived data. Metadata definition provides information about the distinct items, such as means of creation, purpose of the data, time and date of creation, creator or author of data, placement on a network (electronic form) where the data was created, what standards used, etc. There are generally two types of metadata: structural/control metadata and guide metadata. Structural metadata is used to describe the structure of the data such as tables, columns and indexes. Guide metadata is used to help humans find specific items and is usually expressed as a set of keywords in a natural language. Metadata 618 may also include the output of a hash function, for example MD-5 (Message-Digest Algorithm 5) or SHA-2, so that the integrity of the data file can be checked. Additionally, Metadata 618 may also include an encryption key or a link to obtain an encryption key, so that the data may be secured from unauthorized access.

Encapsulation

A metadata encapsulation, container or wrapper format is a metadata file format whose specification describes how data and metadata are stored. A program that can identify and open a container file might not be able to decode the contained data. This may happen if the opening program lacks the required decoding algorithm, or the metadata does not provide enough information. By definition, a container format could wrap any kind of data. Though there are a few examples of such file formats (e.g., DDL files), most container formats are specialized for the specific requirements of the data. For example, a popular family of containers is found among multimedia file formats. Since audio and video streams can be coded and decoded with many different algorithms, a container format can be used to provide a single file to the user.

The container file is used to identify different data types. Simpler container formats can contain different types of encoding, while more advanced container formats can support multiple audio and video streams along with the synchronization information needed to play back the various streams together. In most cases, the file header, most of the metadata and the synchro chunks are specified by the container format (for example container formats exist for optimized, low-quality, internet video streaming which, for example, differs from high-quality DVD streaming requirements).

Figure 7:
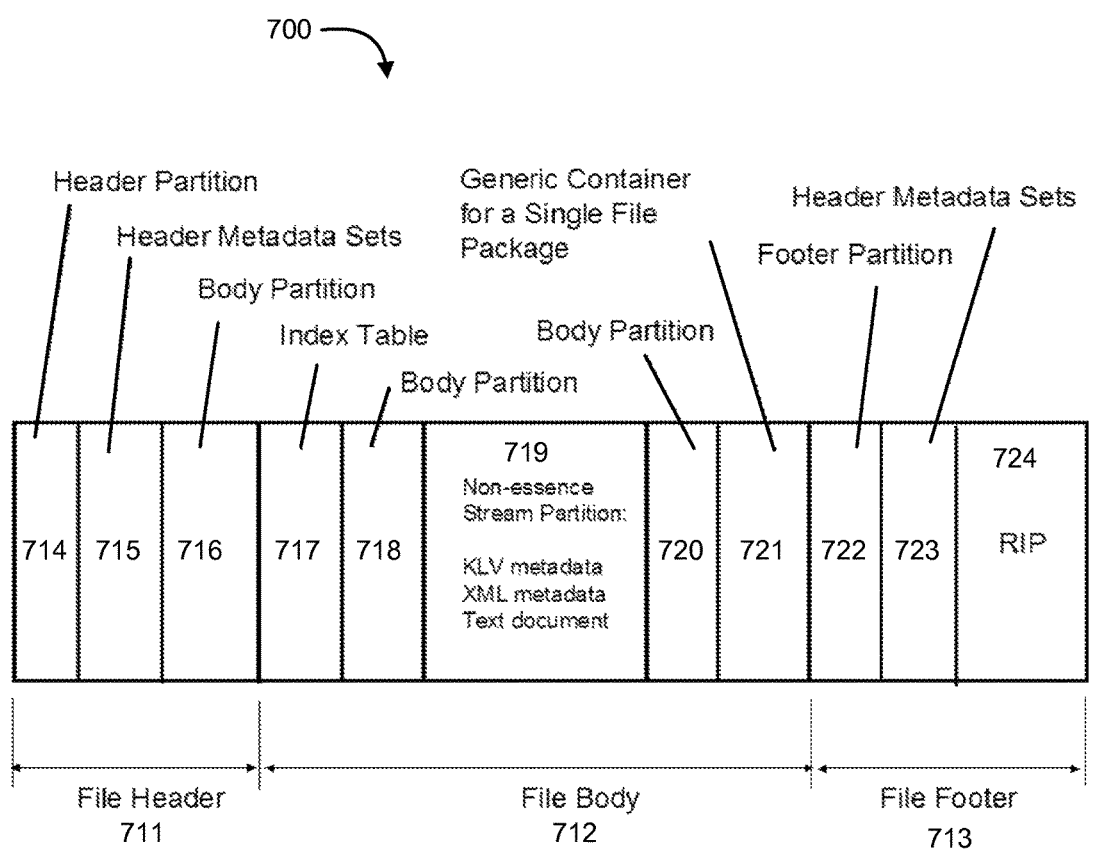
FIG. 7 is a block diagram depicting an example of a Material Exchange Format (MXF) data stream container for use with a client-server library system for archiving image and video data, in accordance with aspects of the invention.

FIG. 7 is a block diagram showing an example of a Material Exchange Format (MXF) image wrapper for use in an embodiment of the client-server library system for archiving image and video data. Image wrapper 700 has three main sections: file header 711, file body 712 and file footer 713. The particular fields in each section of the MXF image wrapper 700 are provided in Table 1 and described, for example, in "The MXF Book", edited by Nick Wells, published by

TABLE 1

FILE HEADER (711)
    Header Partition (714)
    Header Metadata Sets (715)
    Body Partition (716)
FILE BODY (712)
    Index Table (717)
    Body Partition (718)
    Non-essence Stream Partition (719)
    Body Partition (720)
    Generic Container (721)
FILE FOOTER (713)
    Footer Partition (722)
    Header Metadata Sets (723)
    Random Index Pack (724)

Elsevier, © 2006, page 39. Material Exchange Format (MXF) is a container (or wrapper) format which supports a number of different streams of coded "essence", encoded with any of a variety of codecs, together with a metadata wrapper which describes the material contained within the MXF file. The metadata carried by MXF includes structural metadata and descriptive metadata. Structural metadata relates to the structure and capabilities of the MXF file and is generally required for proper decoding. Some examples of structural metadata are descriptions of essence types, information to help synchronize playout of audio and video, and content length. Descriptive metadata gives information about the program content in the file and is not essential for decoding. Some examples of descriptive metadata are program title, actors, and scene descriptions. The essence in MXF files may itself carry data, such as vertical blanking interval data used for carriage of Closed Captioning and other purposes.

Figure 8:
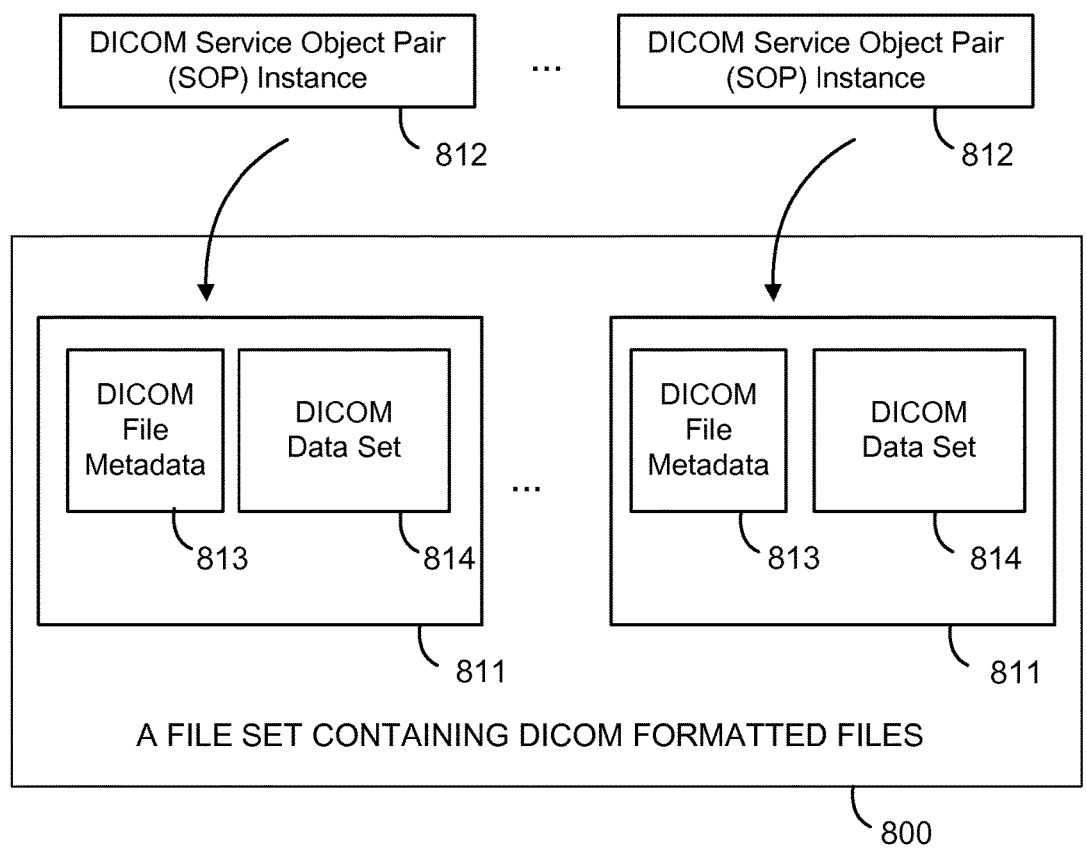
FIG. 8 is a block diagram depicting an example of a Digital Imaging and Communications in Medicine (DICOM) data file, for use with a client-server library system for archiving image and video data, in accordance with aspects of the invention.

FIG. 8 is a block diagram showing another exemplary image wrapping format, the Digital Imaging and Communications in Medicine (DICOM), for use with a client-server library system for archiving image and video data. DICOM file set 800 includes multiple files 811, each containing one DICOM Service Object Pair (SOP) instance 812. Each DICOM SOP file 811 includes DICOM file metadata 813 and a DICOM data set 814. DICOM metadata 813 comprises identifying information on the encapsulated DICOM data set 814. The data set 814 includes image data to be encapsulated.

DICOM is a standard for handling, storing, printing, and transmitting information in medical imaging. It includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, servers, workstations, printers, and network hardware from multiple manufacturers into a picture archiving and communication system. The different devices come with DICOM conformance statements which state the DICOM classes that they support. DICOM has been widely adopted by hospitals, clinics, and doctor offices.

DICOM data object consists of a number of attributes, including items such as name, ID, etc., and also one special attribute containing the image pixel data (i.e., logically, the main object has no "header" as such—merely a list of attributes, including the pixel data). A single DICOM object can only contain one attribute containing pixel data. For many modalities, this corresponds to a single image. The attribute may contain multiple "frames", allowing storage of video loops or other multi-frame data. Another example is nuclear medicine (NM) data, where an NM image by definition is a multi-dimensional multi-frame image. In these cases, three-dimensional or four-dimensional data can be encapsulated in a single DICOM object. Pixel data can be compressed using a variety of standards, including JPEG, JPEG 2000, and Run-length encoding (RLE).

Figure 9:
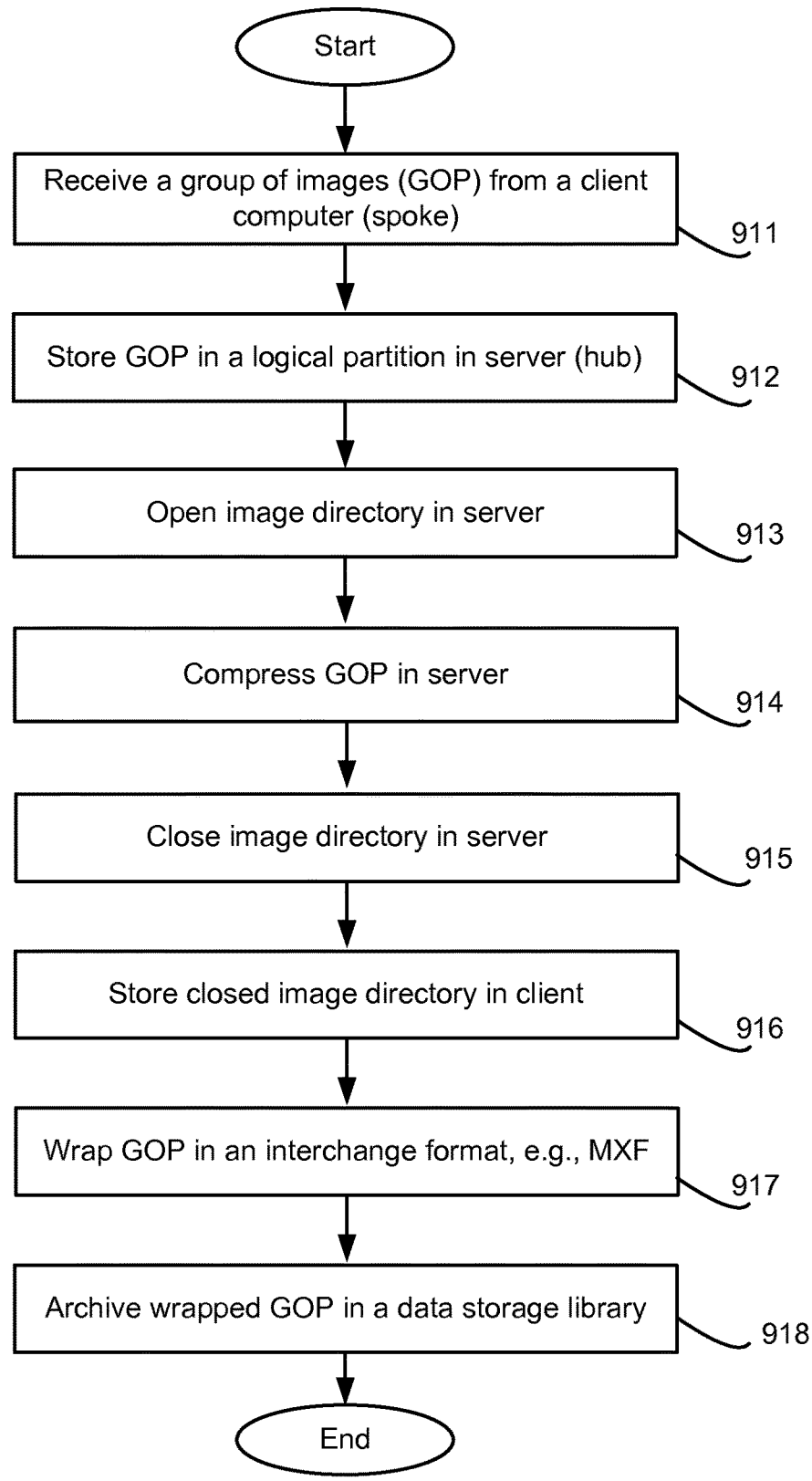
FIG. 9 is a flow chart of an exemplary process for encapsulating a group of images and preparing the encapsulated images for archiving, in accordance with aspects of the invention.

FIG. 9 is a flow diagram of an exemplary process for encapsulating a group of images for archiving in a client-server library system, according to aspects of the invention. At block 911, the server 612 receives a group of images 614 from the client 611. The server 612 stores the images 614 in a logical partition 620 in the server, at block 912. The server 612 also opens an image directory 619, at block 913. The images 614 may be compressed to reduce the amount of storage occupied by them, per block 914. The image directory 619 in the server 612 is closed (915) and its copy 615 is saved in the client 611, per block 916. At block 917, the group of images 614 are wrapped in an image interchange format such as Material Exchange Format (MXF), Digital Imaging and Communications in Medicine (DICOM), Tape Archive (TAR), and GZIP (GZ). At block 918, the wrapped images are archived in the storage library 613.

Figure 10:
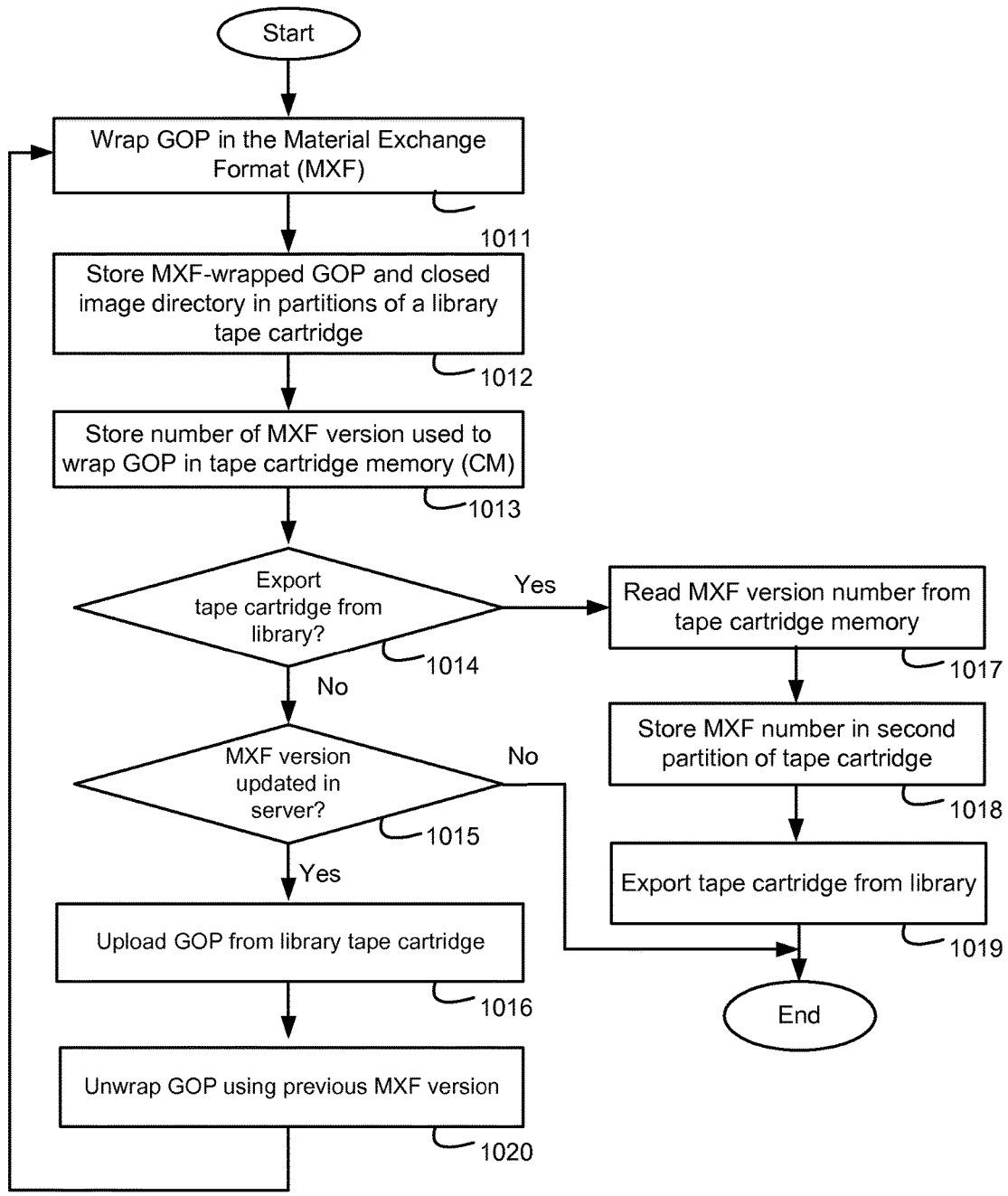
FIG. 10 is a flow chart of a more detailed and exemplary process for archiving a group of images in a client-server library system, in accordance with aspects of the invention.

FIG. 10 is a flow diagram of a more detailed exemplary process for archiving a group of images in a client-server library system, according to aspects of the invention, where the version of MXF is checked for possible updating, so that archived images are never so old and stale that the software for unwrapping and accessing the images no longer exists. In this exemplary embodiment, the Material Exchange Format (MXF) is used for the image encapsulation and the data storage library is a tape library system. At block 1011, the group of images 614 are wrapped in an MXF wrapper as described above with reference to FIG. 7. The closed image directory 622 may be stored in a first partition of a library tape cartridge, and the image wrapper 621 may be stored in a second partition of that same library tape cartridge, at block 1012. An example of a partitioned tape cartridge is the IBM Linear Tape Open (LTO) tape cartridge, Generation-5. The version number of the MXF utility may be stored in a memory device associated with the tape cartridge, as shown by block 1013. At block 1014, the process determines whether the tape cartridge needs to be exported from the library system at this time. If so, the MXF version number is read from the memory device (block 1017) and stored in a second data partition of the tape cartridge and/or cartridge memory 402 (block 1018) before the tape is exported from the library (block 1019).

If the tape cartridge does not need to be exported, then the exemplary process checks whether the MXF software version has recently been updated in the server 612, per block 1015. If the MXF software version has not been changed, then the archiving of the target images is completed. Otherwise, the archived images 614 are uploaded from the tape library system, at block 1016. The images 614 are unwrapped at block 1020 using the previous MXF version (before the MXF version update). The images 614 are then re-encapsulated with their metadata using the new MXF version, at block 1011.

The subject matter described above is provided by way of illustration only and should not be construed as limiting. Various modifications and substitutions of the described components and operations can be made by those skilled in the art without departing from the spirit and scope of the present invention defined in the following claims, the scope of which is to be accorded the broadest interpretation so as to encompass such modifications and equivalent structures. For example, audio, text, spreadsheets, and databases could be encapsulated with metadata. Such audio may include information on heart murmurs. Text could include patient medical records and financial. Spreadsheets and databases may include company or hospital-wide activities. As will be appreciated by those skilled in the art, the systems, methods, and procedures described herein can be embodied in a programmable computer, computer executable software, or digital circuitry. The software can be stored on computer readable media. For example, computer readable media can include a floppy disk, RAM, ROM, hard disk, removable media, flash memory, a "memory stick", optical media, magneto-optical media, CD-ROM, etc.

What is claimed is:
1. An information archive system comprising:
   at least one processor device;
   a plurality of memory devices in communication with the least one processor device;
   a plurality of storage devices in communication with the least one processor device;
   a plurality of clients in communication with the least one processor device;
   a server, having an image directory in communication and association with a closed image directory and an information logical partition and an information directory included in the information logical partition, in communication with the processor device and the plurality of clients;
   a library coupled to the server and in communication with the at least one processor device, wherein the least one processor device:
      receives a plurality of images in the server to be archived from one of the plurality of clients,
      stores the plurality of images that are received from one of the plurality of clients and the image directory in the information logical partition of the server;
      opens the image directory in the server;
      compresses pixel data of the plurality of images in the server using a Run-Length Encoding (RLE) standard, the pixel data including pixels of multi-frame data;
      closes the image directory in the server;
      stores the image directory, which was closed, in one of the plurality of clients as a closed image directory;
      encapsulates the plurality of images and metadata associated with the plurality of images in a data wrapper using a Material Exchange Format (MXF), and storing the plurality of images and the metadata that are encapsulated in one of the plurality of storage devices, wherein the data wrapper describes how the information and the metadata are stored; and
      archives the data wrapper and a closed copy of the information directory in the library, when using the MXF format for encapsulating the plurality of images and the metadata associated with the plurality of images in the data wrapper performs each of:
   updating the MXF format in the server,
   storing the closed image directory in a first partition of a library tape cartridge and the data wrapper in a second partition of the library tape cartridge,
   storing a version number of the MXF format in one of the plurality of storage devices associated with the library tape cartridge, the version number corresponding to an MXF software version used to read the MXF format,
   if the library tape cartridge should be exported:
      reading the version number of the MXF format from a memory device and storing the version number of the MXF format in the second partition of the library tape cartridge prior to exporting the library tape cartridge from the library,
      exporting the library tape cartridge from the library,
   if the library tape cartridge should not be exported:
      determining if the MXF software version used to read the MXF format has been updated in the server, wherein, if the MXF software version has been updated in the server such that the server is executing a newer MXF software version to read the plurality of images, the data wrapper that is archived is uploaded, the plurality of images are unwrapped using a previous MXF software version executed by the server, and the plurality of images and metadata are re-encapsulated with the updated MXF software version; and
      updating each version number of the MXF of the data wrapper that is archived to allow for unwrapping the data wrapper.

2. The archive system of claim 1, wherein the plurality of images that are encapsulated is stored in the library as a closed information file.

3. The archive system of claim 1, wherein the plurality of images metadata includes content information.

4. The archive system of claim 3, wherein the content information includes title, person and scene descriptions.

5. The archive system of claim 1, storing each version number of the MXF of the data wrapper associated with the one of the plurality of storage devices used for storing the plurality of images and the metadata that are encapsulated.

6. The archive system of claim 1, wherein the library is a tape library having at least one tape media for storing the plurality of images.

7. The archive system of claim 1, wherein the library is an optical storage library having at least one optical media for storing the information.

8. The archive system of claim 7, wherein the optical media is selected from a group of a plurality of storage media, wherein the plurality of storage media include at least an optical tape, an optical disk, a removable magnetic disk drive, and digital video disk (DVD).

9. The archive system of claim 1, wherein the library is a disk storage library having at least one disk media for storing the plurality of images.

10. The archive system of claim 1, wherein the library is a solid state memory library having at least one solid state memory for storing the plurality of images.

11. The archive system of claim 1, wherein the library includes an archive media directory for locating a particular media when storing and retrieving the plurality of images in the library.

12. The archive system of claim 1, wherein the library is used in a redundant storage system for recovering lost data.

13. The archive system of claim 1, wherein the plurality of images in the server are exported to the library to accommodate a plurality of new images from one of the plurality of clients when a server storage threshold is reached.

14. The archive system of claim 1, wherein the plurality of images are selected from the group comprising still images, segments of a video stream, an entire video stream, audio, text, spreadsheets, and databases.

15. A computer implemented method for archiving information in a system having a plurality of clients, a server and a library, the method comprising:
   receiving a plurality of images in the server to be archived from one of the plurality of clients,
   storing the plurality of images that are received from one of the plurality of clients and an image directory in an information logical partition of the server;
   opening the image directory in the server;
   compressing pixel data of the plurality of images in the server using a Run-Length Encoding (RLE) standard, the pixel data including pixels of multi-frame data;
   closing the image directory in the server;
   storing the image directory, which was closed, in one of the plurality of clients in a closed image directory;
   encapsulating the plurality of images and metadata associated with the plurality of images in a data wrapper using a Material Exchange Format (MXF), and storing the plurality of images and the metadata that are encapsulated in one of the plurality storage devices, wherein the data wrapper describes how the information and the metadata are stored; and
   archiving the data wrapper and a closed copy of an information directory in the library,
   when using the MXF format for encapsulating the plurality of images and the metadata associated with the plurality of images in the data wrapper performing each of:
      updating the MXF format in the server,
      storing the closed image directory in a first partition of a library tape cartridge and the data wrapper in a second partition of the library tape cartridge,
      storing a version number of the MXF format in one of the plurality of storage devices associated with the library tape cartridge, the version number corresponding to an MXF software version used to read the MXF format,
      if the library tape cartridge should be exported:
         reading the version number of the MXF format from a memory device and storing the version number of the MXF format in the second partition of the library tape cartridge prior to exporting the library tape cartridge from the library,
         exporting the library tape cartridge from the library,
      if the library tape cartridge should not be exported:
         determining if the MXF software version used to read the MXF format has been updated in the server such that the server is executing a newer MXF software version to read the plurality of images, wherein, if the MXF software version has been updated in the server, the data wrapper that is archived is uploaded, the plurality of images are unwrapped using a previous MXF software version executed by the server, and the plurality of images and metadata are re-encapsulated with the updated MXF software version; and updating each version number of the MXF of the data wrapper that is archived to allow for unwrapping the data wrapper.

16. A computer program product for archiving information in a system having a plurality of clients, a server and a library, the program product comprising a non-transitory computer readable storage medium having program code embodied therein and operable for:

receiving a plurality of images in the server to be archived from one of the plurality of clients, storing the plurality of images that are received from one of the plurality of clients and an image directory in an information logical partition of the server;

opening the image directory in the server;

compressing pixel data of the plurality of images in the server using a Run-Length Encoding (RLE) standard, the pixel data including pixels of multi-frame data;

closing the image directory in the server;

storing the image directory, which was closed, in one of the plurality of clients in a closed image directory;

encapsulating the plurality of images and metadata associated with the plurality of images in a data wrapper using a Material Exchange Format (MXF), and storing the plurality of images and the metadata that are encapsulated in one of the plurality of storage devices, wherein the data wrapper describes how the information and the metadata are stored; and archiving the data wrapper and a closed copy of an information directory in the library, when using the MXF format for encapsulating the plurality of images and the metadata associated with the plurality of images in the data wrapper performing each of:

updating the MXF format in the server, storing the closed image directory in a first partition of a library tape cartridge and the data wrapper in a second partition of the library tape cartridge, storing a version number of the MXF format in one of the plurality of storage devices associated with the library tape cartridge, the version number corresponding to an MXF software version used to read the MXF format, if the library tape cartridge should be exported:
reading the version number of the MXF format from a memory device and storing the version number of the MXF format in the second partition of the library tape cartridge prior to exporting the library tape cartridge from the library,
exporting the library tape cartridge from the library, if the library tape cartridge should not be exported:
determining if the MXF software version used to read the MXF format has been updated in the server such that the server is executing a newer MXF software version to read the plurality of images, wherein, if the MXF software version has been updated in the server, the data wrapper that is archived is uploaded, the plurality of images are unwrapped using a previous MXF software version executed by the server, and the plurality of images and metadata are re-encapsulated with the updated MXF software version; and updating each version number of the MXF of the data wrapper that is archived to allow for unwrapping the data wrapper.

* * * * *